US011327000B2

(12) United States Patent
Karimi et al.

(10) Patent No.: US 11,327,000 B2
(45) Date of Patent: May 10, 2022

(54) DETECTING SATURATION LEVELS OF A CORE SAMPLE USING MAGNETIC FIELDS

(71) Applicants: Saudi Arabian Oil Company, Dhahran (SA); King Abdullah University of Science and Technology, Thuwal (SA)

(72) Inventors: Muhammad Akram Karimi, Thuwal (SA); Muhammad Ayub, Dhahran (SA); Muhammad Arsalan, Dhahran (SA); Atif Shamim, Thuwal (SA)

(73) Assignees: Saudi Arabian Oil Company, Dhahran (SA); King Abdullah University of Science and Technology, Thuwal (SA)

( * ) Notice: Subject to any disclaimer, the term of this patent is extended or adjusted under 35 U.S.C. 154(b) by 1025 days.

(21) Appl. No.: 15/984,471

(22) Filed: May 21, 2018

(65) Prior Publication Data
US 2019/0353573 A1    Nov. 21, 2019

(51) Int. Cl.
*G01N 15/08*    (2006.01)
*G01R 33/02*    (2006.01)
*G01N 33/24*    (2006.01)

(52) U.S. Cl.
CPC ........... *G01N 15/082* (2013.01); *G01N 33/24* (2013.01); *G01R 33/02* (2013.01)

(58) Field of Classification Search
CPC .... G01V 3/08; G01V 3/081; G01V 3/10–108; G01N 33/24; G01N 15/082; G01N 27/72; G01N 27/74; G01R 33/02; G01R 33/0206; G01R 33/028; G01R 33/12; G01R 33/1215
See application file for complete search history.

(56) References Cited

U.S. PATENT DOCUMENTS 4,490,676 A    12/1984    Davis, Jr. et al.
4,499,418 A    2/1985    Helms et al.
(Continued)

FOREIGN PATENT DOCUMENTS

WO    WO-2015/200789 A1    12/2015
WO    WO-2015200789 A1 *    12/2015    .............. G01V 3/32
WO    WO-2017/040102 A1    3/2017

OTHER PUBLICATIONS

International Search Report for PCT/IB2018/057351, 6 pages (dated Dec. 10, 2018).
(Continued)

*Primary Examiner* — Huy Q Phan
*Assistant Examiner* — David B Frederiksen
(74) *Attorney, Agent, or Firm* — Choate, Hall & Stewart LLP; Charles E. Lyon; Peter A. Flynn

(57) ABSTRACT

An example system is configured to detect saturation levels of a target, such as a core sample of a reservoir, using magnetic fields generated by hydrophilic magnetic nanoparticles within the target. The target contains both a hydrocarbon, such as oil or gas, and a mixture comprised of water and the hydrophilic magnetic nanoparticles. The system includes magnetic field detectors for spatial distribution across a dimension of the target. The magnetic field detectors are configured to detect a magnetic field associated with the hydrophilic magnetic nanoparticles. A data processing system is configured—for example, programmed—to determine a saturation profile of the target based on the magnetic field.

22 Claims, 8 Drawing Sheets

(56) References Cited

U.S. PATENT DOCUMENTS

| | | | |
|---|---|---|---|
| 4,543,821 A | 10/1985 | Davis, Jr. | |
| 5,341,101 A | 8/1994 | Maerefat et al. | |
| 5,389,883 A | 2/1995 | Harper | |
| 5,485,743 A | 1/1996 | Taherian et al. | |
| 5,493,226 A | 2/1996 | Honarpour et al. | |
| 6,586,371 B1* | 7/2003 | Maroy | C09K 8/12 507/120 |
| 8,640,529 B2 | 2/2014 | Sinha | |
| 9,335,273 B2 | 5/2016 | Botto et al. | |
| 9,650,891 B2 | 5/2017 | Reid et al. | |
| 9,804,105 B2 | 10/2017 | Karimi et al. | |
| 9,909,411 B2* | 3/2018 | Carlson | E21B 17/04 |
| 10,151,817 B2* | 12/2018 | Hogendoorn | G01F 1/716 |
| 10,481,291 B2* | 11/2019 | Appel | G01R 33/561 |
| 2008/0150518 A1 | 6/2008 | Becker et al. | |
| 2009/0179649 A1 | 7/2009 | Schmidt et al. | |
| 2009/0184706 A1* | 7/2009 | Durie | G01N 27/745 324/202 |
| 2012/0235074 A1* | 9/2012 | Iftime | H01F 1/0054 252/62.53 |
| 2013/0002258 A1* | 1/2013 | Ligneul | E21B 47/06 324/376 |
| 2013/0033272 A1 | 2/2013 | Folgeroe et al. | |
| 2013/0091941 A1* | 4/2013 | Huh | E21B 49/008 73/152.08 |
| 2013/0125630 A1* | 5/2013 | Collins | E21B 43/20 73/64.56 |
| 2013/0293026 A1* | 11/2013 | Miyamoto | G01V 3/10 307/104 |
| 2014/0007667 A1* | 1/2014 | Haggerty | G01N 33/241 73/152.11 |
| 2014/0021345 A1* | 1/2014 | Maucec | G01N 15/082 250/260 |
| 2014/0182737 A1 | 7/2014 | Jones et al. | |
| 2014/0323363 A1 | 10/2014 | Perriat et al. | |
| 2015/0346126 A1* | 12/2015 | Jakkula | G01R 27/06 324/637 |
| 2015/0362331 A1* | 12/2015 | Sanchez | A63B 60/16 702/153 |
| 2015/0376493 A1 | 12/2015 | Huh et al. | |
| 2016/0312602 A1* | 10/2016 | Carlson | E21B 17/04 |
| 2017/0059492 A1* | 3/2017 | Karimi | G01N 33/2823 |
| 2017/0248506 A1 | 8/2017 | Gupta et al. | |
| 2017/0350830 A1 | 12/2017 | Karimi et al. | |
| 2017/0361376 A1 | 12/2017 | Murugesan et al. | |
| 2018/0011033 A1 | 1/2018 | Karimi et al. | |
| 2018/0196897 A1* | 7/2018 | Filippov | G06F 30/20 |

OTHER PUBLICATIONS

Potter, D.K. et al., Quantifying the effects of core cleaning, core flooding and fines migration using sensitive magnetic techniques: implications for permeability determination and formation damage, Petrophysics, 52(6): 444-451 (2011).
Written Opinion for PCT/IB2018/057351, 9 pages (dated Dec. 10, 2018).
U.S. Appl. No. 15/984,469, SA2106.
U.S. Appl. No. 15/907,575, SA2086.
Agar Corporation, OW-200 Series Oil/Water Meters Liquid/Liquid Concentration, Process Measurement & Control Solutions, 3 pages [Retrieved Online Jun. 19, 2018], URL: http://www.agarcorp.com/literature/ow200.html.
Al-Taweel, A. B. and Barlow, S. G., Field Testing MultiPhase Meters, Society of Petroleum Engineers Inc. SPE 56583, 16 pages (1999).
Alvarado, F.E.,et al., Visualization of three phases in porous media using micro computed tomography, paper SCA2003-21 presented at the International Symposium of Society of Core Analysts, Pau, France (Sep. 21-24, 2003).
Amyx, J.W. et al.. Petroleum Reservoir Engineering, Physical Properties, McGraw Hill Book Co., New York, Indian Edition, 629 pages (1960).
Ayub, M. and Bentsen, R. G., An Apparatus for Simultaneous Measurement of Dynamic Saturation and Capillary Pressure Profiles, Paper 99-72: presented at the CSPG and Petroleum Society Joint Convention, Digging Deeper, Finding a Better Bottom Line, Calgary, Alberta, Canada, 13 pages (Jun. 14-18, 1999).
Ayub, M. and Bentsen, R. G., Measurement of Dynamic Saturation Profiles, Journal of Canadian Petroleum Technology, 39(9): 54-61 (2000).
Bail, P.T. and Marsden, S.S., Saturation distribution in a linear system during oil displacement, Producers Monthly, 21(8): 22-32 (1957).
Brost, D.F. and Davis, L.A., Determination of oil saturation distribution in field cores by microwave spectroscopy, SPE 10110, presented at the 56th Annual Fall Technical Conference and Exhibition, Society of Petroleum Engineers of AIME, San Antonio, TX, 19 pages (Oct. 5-7, 1981).
Caudle, B.H. et al.. Further developments in the laboratory determination of relative permeabilities, Trans. AIME, 192: 145-150 (1951).
Chatenever, A. and Calhoun, J.C. Jr., Visual examinations of fluid behavior in porous media—Part 1, Trans. AIME, 195: 149-156 (1952).
Craig, F.F., Jr., The Reservoir Engineering Aspects of Waterflooding, Monograph vol. 3 of the Henry L. Doherty Series, Millet the Printer, Dallas, TX, 141 pages (1971).
Davis, L.A. Jr., Computer-controlled measurement of laboratory areal flood saturation distributions, SPE 12037, presented at the 58th Annual Fall Technical Conference and Exhibition, Society of Petroleum Engineers of AIME, San Francisco, CA, 8 pages (Oct. 5-8, 1983).
Davis, L.A. Jr., VHF electrical measurement of saturation in laboratory floods, Paper SPE No. 8847 presented at the First Joint SPE/DOE Symposium on Enhanced Oil Recovery, Tulsa, Oklahoma, 10 pages (Apr. 20-23, 1980).
Dongzhi, Z., Analysis of Multi-factor Influence on Measurement of Water Content in Crude Oil and Its Prediction Model, Proceedings of the 27th Chinese Control Conference, Kunming, Yunnan, China, 6 pages (Jul. 16-18, 2008).
Essiflo, Water Cut Meter, 5 pages [Retrieved Online Jun. 19, 2018], URL: http://eesiflo.com/water-cut-meter.html.
Geffen, T.M. and Gladfelter, R.E., A note on the X-ray absorption method of determining fluid saturations in cores, Petroleum Transactions, AIME, 195: 322-323 (1952).
Honarpour, M. and Mahmood, S.M., Relative permeability measurements: An Overview, Journal of Petroleum Technology, SPE 18565: 963-966 (Aug. 1988).
Honarpour, M., et al., Relative Permeability of Petroleum Reservoir, CRC Press, Inc., Boca Raton, FL, USA, 154 pages (1986).
Joshi, K.K. et al., Non-destructive Microstrip Resonator Technique for the measurement of moisture / permittivity in crude oil, Proceedings of the XXVIIIth URSI General Assembly, New Delhi, India, 8 pages (2005).
Kantzas, A., Investigation of physical properties of porous rocks and fluid flow phenomena in porous media using computer assisted tomography, In Situ, 14(1): 77-132 (1990).
Karimi, M.A. et al., Design and Dynamic Characterization of an Orientation Insensitive Microwave Water-Cut Sensor, IEEE Transactions on Microwave Theory and Techniques, 66(1): 530-539 (2018).
Karimi, M.A. et al., Low Cost and Pipe Conformable Microwave-Based Water-Cut Sensor, IEEE Sensors Journal, 16(21): 7636-7645 (2016).
Laird, A.D.K. and Putman, J.A., Fluid saturation in porous media by X-ray techniques, Petroleum Transactions, AIME, 192: 275-284 (1951).
Leverett, M.C. and Lewis, W.B., Steady flow of gas-oil-water mixtures through unconsolidated sands, Petroleum Transactions, AIME, 142: 107-116 (1941).
McKerricher, G. et al., Crude Oil Water-Cut Sensing with Disposable Laser Ablated and Inkjet Printed RF Microfluidics, IMS, 3 pages (2014).

(56) References Cited

OTHER PUBLICATIONS

Mohamed, A.-M. O. et al., Effect of salinity and temperature on water cut determination in oil reservoirs, Journal of Petroleum Science and Engineering, 40: 177-188 (2003).

Nyfors, E. G., Cylindrical Microwave Resonator Sensors for Measuring Materials Under Flow, Helsinki University of Technology, Report S243, 181 pages (May 2000).

Parker, A. and Joshi, S., M-Flow Technologies Ltd, 16040: Non-Intrusive Water Cut Measurement Based on a Composite Construction Material Platform, UPM Forum, Upstream Production Measurement, Houston, TX, 18 pages (Feb. 24-25, 2016).

Parsons, R.W., Microwave Attenuation—A new tool for monitoring saturations in laboratory flooding experiments, Society of Petroleum Engineers Journal, 15(4): 302-310 (1975).

Roxar, Roxar Watercut meter, Product Data Sheet, Emerson Process Management, 11 pages (Apr. 4, 2016). URL: http://www2.emersonprocess.com/siteadmincenter/PM%20Roxar%20Documents/Roxar%20Watercut%20meter%20Data%20Sheet.pdf.

Schematic drawing of core-flooding setup, ResearchGate, 4 pages [Retrieved Mar. 15, 2018]. URL: https://www.researchgate.net/figure/Schematic-drawing-of-core-flooding-setup-The-isolat . . . .

Stanley, M., Magnetometers come in multiple flavors, Me and My Smarter World, NXP, 4 pages (Mar. 4, 2011). URL: <https://blog.nxp.com/sensors/magnetometers-come-in-multiple-flavors>. [Retrieved Apr. 18, 2018].

Sun, X. et al., Application of Nanoparticles in Enhanced Oil Recovery: A Critical Review of Recent Progress, Energies, 10(345): 33 pages (2017).

Swanson, B.F., Visualizing Pores and Nonwetting Phase in Porous Rock, Journal of Petroleum Technology, 10-18 (1979).

Tošic, D. and Potrebic, M., Compact Multilayer Bandpass Filter with Modified Hairpin Resonators, Journal of Microelectronics, Electronic Components and Materials, 42(2): 123-130 (2012).

Weatherford International, Water-Cut Meters, 3 pages [Retrieved Online Jun. 19, 2018], URL: https://www.weatherford.com/en/products-and-services/production/flow-measurement/water-cut-meters.

Willhite, G.P., Waterflooding, Society of Petroleum Engineers, Richardson, TX., USA, SPE Textbook Series, vol. 3, 333 pages (1986).

Wylie, S.R. et al., RF sensor for multiphase flow measurement through an oil pipeline, Meas. Sci. Technol., 17: 2141-2149 (2006).

Yadav, G.D. et al., Microscopic distribution of wetting and nonwetting phases in sandstones during immiscible displacements, SPE Reservoir Engineering, 2: 137-147 (1987).

Yang, Y.S. et al., The Design, Development and Field Testing of a Water-Cut Meter Based on a Microwave Technique, Society of Petroleum Engineers, SPE 20697: 775-782 (1990).

\* cited by examiner

DETECTING SATURATION LEVELS OF A CORE SAMPLE USING MAGNETIC FIELDS

TECHNICAL FIELD

This specification relates generally to example techniques for detecting saturation levels of a core sample using magnetic fields generated by nanoparticles within the core.

BACKGROUND

A process known as waterflooding is used to displace and to produce hydrocarbons, such as oil or gas, from a reservoir when natural energy of the reservoir is insufficient to force the hydrocarbons into a well. Waterflooding may be performed in the field by pumping liquid, such as water, into the reservoir through one or more injection wells.

The resulting displacement of water for hydrocarbons caused by waterflooding may be modeled in a laboratory before actual field deployment. For this purpose, small pieces of rock, known as cores, are extracted from a rock formation in the reservoir. The cores are used to mimic the waterflooding process in the laboratory. Experiments performed in the laboratory, known as coreflooding, may be used to determine saturation profiles for the core and for the reservoir.

In an example coreflooding experiment, fluid such as water is injected into a core extracted from the reservoir. Measurements are taken based on the fluid injection in order to estimate the performance of the reservoir when subjected to waterflooding. In some cases, waterflooding parameters may be adjusted based on measurements taken during the coreflooding process in order to affect hydrocarbon yield from the reservoir.

SUMMARY

An example system is configured to detect saturation levels of a target, such as a core sample of a reservoir, using magnetic fields generated by hydrophilic magnetic nanoparticles within the target. The target contains both a hydrocarbon, such as oil or gas, and a mixture comprised of water and the hydrophilic magnetic nanoparticles. The system includes magnetic field detectors for spatial distribution across a dimension of the target. The magnetic field detectors are configured to detect a magnetic field associated with the hydrophilic magnetic nanoparticles. A data processing system is configured—for example, programmed—to determine a saturation profile of the target based on the magnetic field. The example system may include one or more of the following features, either alone or in combination.

The hydrophilic magnetic nanoparticles may have a stronger affinity with water than with the hydrocarbon. The hydrophilic magnetic nanoparticles may be immiscible in hydrocarbons such as crude oil or natural gas condensates.

The data processing system may be configured to perform operations that include obtaining first data based on the magnetic field, where the first data represents a magnitude of the magnetic field and a direction of the magnetic field, processing the first data to determine the saturation profile, and outputting second data representing the saturation profile. The data processing system may be configured to determine, as part of the saturation profile, relative amounts of the hydrocarbon and the water across a dimension of the target.

The saturation profile may include a magnitude component and a direction component. The magnitude component may be indicative of an amount of water in the target. The direction component may be indicative of a direction of flow of the water through the target. The saturation profile may include a temporal component and a spatial component. The temporal component may be indicative of a duration of at least part of the spatial component.

The target may be a core sample of a reservoir formation comprised of porous rock. The core sample may be held by a core holder. The magnetic field detectors may be located on the core holder. The magnetic field detectors may include inductively-coupled coil arranged along a dimension of the target along which fluid flows through the target. The magnetic field detectors may include magnetometers arranged along the dimension of the target along which fluid flows through the target. The magnetometers may be configured to determine, based on the magnetic field, a magnetic field strength vector in three dimensions. The magnetic field strength vector may represent changes in magnetic field strength, direction, of both magnetic field strength and direction across the target.

An example method may be performed to generate a saturation profile of a target, such as a core sample of a reservoir containing a hydrocarbon. The method includes forcing through the target a mixture comprised of water and hydrophilic magnetic nanoparticles to produce within the target a distribution of the mixture and the hydrocarbon. The method also includes detecting a magnetic field associated with the hydrophilic magnetic nanoparticles within the target and generating the saturation profile of the target based on the magnetic field. The saturation profile represents at least part of the distribution. The example method may include one or more of the following features, either alone or in combination.

The hydrophilic magnetic nanoparticles may have a stronger affinity with water than with the hydrocarbon. The hydrophilic magnetic nanoparticles may be immiscible in hydrocarbons such as crude oil or natural gas condensates.

The magnetic field may be detected using magnetic field detectors spatially distributed across a dimension of the target. Generating the saturation profile may be performed using a data processing system and may include obtaining first data based on the magnetic field. The first data may represent a magnitude of the magnetic field and a direction of the magnetic field. Generating the saturation profile may also include processing the first data to determine the saturation profile and outputting second data representing the saturation profile. Generating the saturation profile may include determining, as part of the saturation profile, relative amounts of the hydrocarbon and water across a length of the target.

The saturation profile may include a magnitude component and a direction component. The magnitude component may be indicative of an amount of water in the target and the direction component may be indicative of a direction of flow of the water through the target. The saturation profile may include a temporal component and a spatial component. The temporal component may be indicative of a duration of at least part of the spatial component.

The target may be a core sample of a reservoir formation comprised of porous rock. The core sample may be held by a core holder. Detecting the magnetic field may be performed by magnetic field detectors located on the core holder. The magnetic field detectors may include inductively-coupled coil arranged along a dimension of the target along which fluid flows through the target. The magnetic field detectors may include magnetometers arranged along the dimension of the target along which the fluid flows through the target. The magnetometers may be configured to determine, based on the magnetic field, a magnetic field strength vector in three dimensions. The magnetic field strength vector may represent changes in magnetic field strength across the target.

The method may include performing a correlation process based on the magnetic field to determine at least one of a direction that fluid is traveling through the core, a speed at which the fluid is traveling through the core, or a content of the fluid contained in an area of the core. At least some of the fluid includes the mixture. In some implementations, using a correlation process it may be possible to improve spatial resolution of the saturation profile relative to methods of determining a saturation profile that do not employ such a correlation process.

Advantages of the system may also include one or more of the following. Including the magnetic field detectors on the core holder may minimize the size of the system in some cases, making the system more compact than other types of coreflooding systems. Detection of the saturation profile may not be affected by the salinity of water used in the mixture, since salt does not affect the magnetic field produced by the hydrophilic magnetic nanoparticles. By placing the inductively-coupled coils, magnetometers, or both on or in a core holder that is conformal to the core, it may be possible to reduce the effects of external magnetic fields on magnetic field measurements. In some implementations, the system may be configured to determine saturation profiles for both consolidated media and unconsolidated media. Consolidated media includes grains that are held together naturally by a cementing process. Unconsolidated media includes grains that are packed but not held together by another substance.

Any two or more of the features described in this specification, including in this summary section, may be combined to form implementations not specifically described in this specification.

At least part of the processes and systems described in this specification may be controlled by executing, on one or more processing devices, instructions that are stored on one or more non-transitory machine-readable storage media. Examples of non-transitory machine-readable storage media include read-only memory (ROM), an optical disk drive, memory disk drive, and random access memory (RAM). At least part of the processes and systems described in this specification may be controlled using a data processing system comprised of one or more processing devices and memory storing instructions that are executable by the one or more processing devices to perform various control operations.

The details of one or more implementations are set forth in the accompanying drawings and the description subsequently. Other features and advantages will be apparent from the description and drawings, and from the claims.

DESCRIPTION OF THE DRAWINGS

Like reference numerals in different figures indicate like elements.

DETAILED DESCRIPTION

Figure 1:
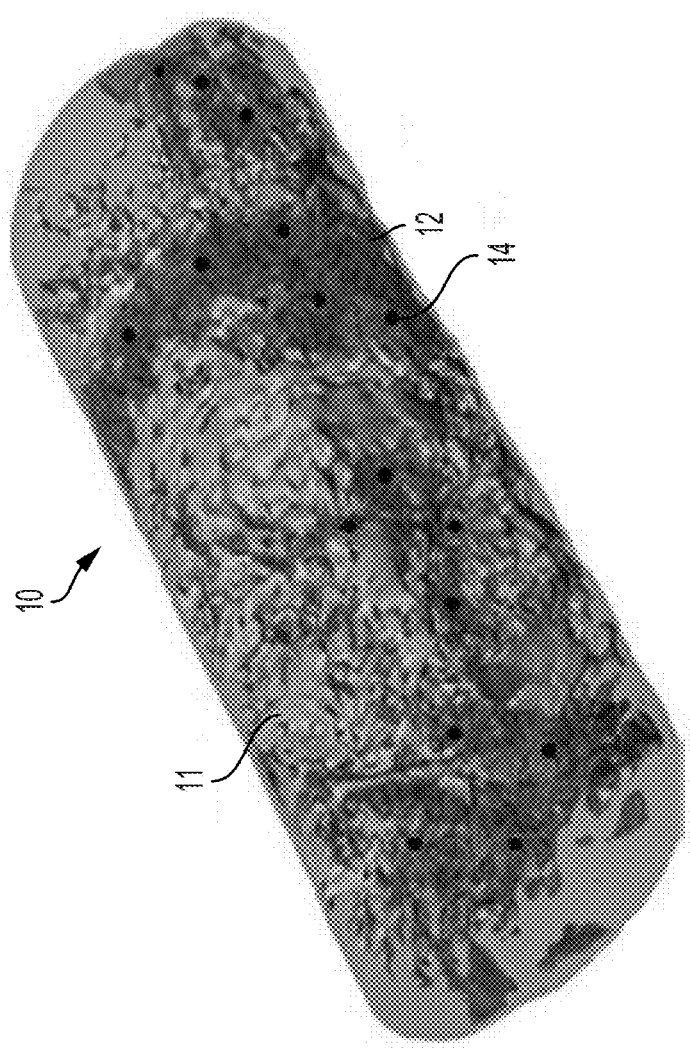
FIG. 1 is a perspective view of an example core.

Effective permeability is a relative measure of the conductance of a porous medium, such as a rock formation, for one fluid phase when the medium is saturated with more than one fluid. Relative permeability (Kr) is the ratio of the effective permeability of one fluid phase to a base permeability. Relative permeability is a parameter used for estimating the performance of a hydrocarbon reservoir, such as an oil or gas reservoir, within a rock formation. For example, relative permeability data may be used to simulate reservoir performance, to estimate past and present reservoir performance, and to estimate future reservoir performance under operating conditions, such as varying temperatures, pressures, and production rates.

Relative permeability is a function of the saturation of a formation. Saturation is based on the relative amounts of water and hydrocarbon, such as gas, oil, or both gas and oil, present in the formation. Factors, such as rock type and fluid properties, may also affect measurements of relative permeability. However, saturation levels typically have the greatest impact on shapes of relative permeability curves for the formation. In some cases, an error in the estimation of a saturation level can introduce an error into the formation's relative permeability data. This error can have a significant negative impact on reservoir performance simulation results.

Coreflooding experiments may be used to estimate the saturation level of a formation by estimating the relative amounts of hydrocarbon and water in a core taken from the formation. Knowing the saturation level, it is possible to estimate the relative permeability of the formation from which the core was taken.

Described in this specification are example systems and associated processes that may be used to implement coreflooding experiments. In an implementation, a mixture comprised of water and hydrophilic magnetic nanoparticles is forced through a target, such as a core, to produce a distribution of the mixture and the hydrocarbon within the core. Magnetic field detectors are spatially distributed across a dimension of the core. For example, the magnetic field detectors may be formed on or held on a core holder. The magnetic field detectors are configured to detect a magnetic field associated with the hydrophilic magnetic nanoparticles. For example, the magnetic field detectors may be configured to detect a magnitude (or strength) of the magnetic field, a direction of the magnetic field, or both a magnitude and a direction of the magnetic field.

A data processing system, such as a computing system, determines a saturation profile of the core based on the magnetic field detected by the magnetic field detectors. The saturation profile may represent at least part of a distribution of hydrocarbon and water in the core. The saturation profile may also provide an indirect view of the pore or grain distribution—referred to as core heterogeneity—along the dimension of the core that fluid travels. That is, the distribution of water within the core may be indicative of the level of heterogeneity of the core and of the reservoir rock from which the core was obtained.

Parts of the system, such as the magnetic field detectors, may be incorporated into an existing core holder. The magnetic field detectors may be fixed to the core holder and, as a result, may occupy little extra space. For example, the magnetic field detectors may include inductively-coupled coil held to and wound around an exterior of the core holder. For example, the magnetic field detectors may include complementary metal-oxide semiconductor (CMOS) magnetometers placed at discrete points on or in an interior sleeve of the core holder.

In an example, the system is noninvasive, is configured to estimate the saturation level of a core, and is configured to obtain dynamic saturation profiles of the core as a function of time and distance along the longitudinal dimension of the core. This information may be used to estimate the relative permeability of the core and of the formation from which the core was extracted. In addition, the dynamic saturation profiles may also be used to observe real time flood-front movement, frontal stability, and viscous fingering within the core. In this regard, a flood-front is stable if it retains the shape of an interface between displaced and displacing fluids as the front moves through a medium.

An example coreflooding experiment employs a mixture comprised of water and hydrophilic magnetic nanoparticles. In some implementations, the hydrophilic magnetic nanoparticles are made of iron (II,III) oxide, an example of which is $Fe_3O_4$. In some implementations, the hydrophilic magnetic nanoparticles may have sizes, such as diameters, in a range of 10 nanometers (nm) to 50 nm. In some implementations, the mixture contains between 0.2 percent-by-weight (wt %) and 0.3 wt % hydrophilic magnetic nanoparticles. The hydrophilic magnetic nanoparticles have a stronger affinity with water than with hydrocarbon. In an example, the hydrophilic magnetic nanoparticles are immiscible in hydrocarbons such as crude oil or natural gas condensates.

FIG. 1 shows an example core 10 that may subjected to a coreflooding experiment using hydrophilic magnetic nanoparticles. Example core 10 is comprised of rock, is porous, and is capable of holding and passing fluid, including hydrocarbon 11 and the mixture 12 of water and hydrophilic magnetic nanoparticles 14.

Figure 2:
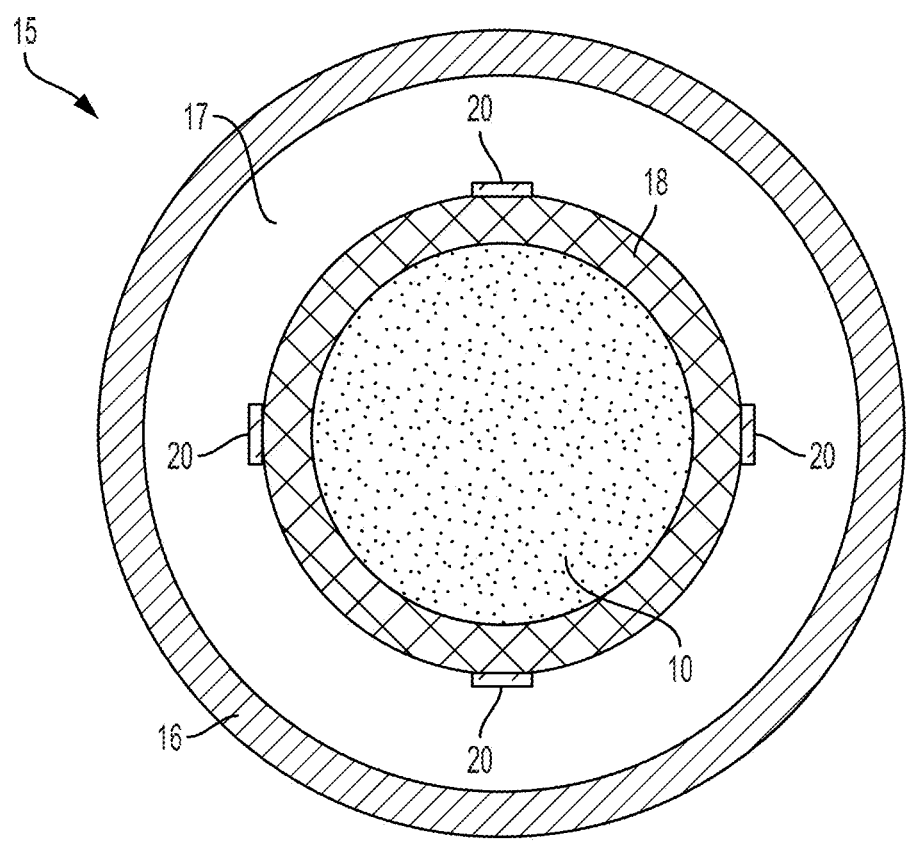
FIG. 2 is a cross-sectional view of an example core holder.

Core 10 may be held by a core holder during the coreflooding experiment. The core holder supports the core and maintains the shape and the integrity of the core. To this end, the core holder may include a frame and a sleeve, both of which conform generally to the shape of the core. In some implementations, the core is cylindrical in shape. Accordingly, the core holder is configured to maintain the cylindrical shape of the core. FIG. 2 shows a cross-section of an example core holder 15 for holding core 10. Example core holder 15 contains a frame 16 and a sleeve 18. Core 10 is also shown in cross-section in FIG. 2.

In some implementations, frame 16 may be made of steel. In some implementations, frame 16 may be made of a non-magnetic material such as polyether ether ketone (PEEK). In some implementations, frame 16 may be made of a combination of fiberglass and epoxy. In some implementations, sleeve 17 may be made of a non-magnetic and non-metallic material. Examples of materials that may form the sleeve include rubber and plastic. The sleeve may provide a seal around the core so that, when under-pressure, no injected fluid bypasses the core.

In the example of FIG. 2, annulus 17 is between frame 16 and sleeve 18 and is filled with a confining liquid. This confining liquid applies pressure to sleeve 18 to hold core 10 tightly within sleeve 18. This pressure produced by the confining liquid and the sleeve confines injected fluids, such as the hydrocarbon and the mixture, within core 10 and prevents those fluids from flowing around the core 10. Thus, all injected fluids flow through core 10 and not around core 10. Any non-conducting, non-magnetic, and stable fluid may be used as the confining liquid. Examples of confining liquids that may be used include water, mineral oil, and hydraulic oil. Selection of these liquids is based on their compressibility factors, their vapor pressures, and their flashpoints. For example, water, mineral oil, and hydraulic oil have lower compressibility factors, higher vapor pressures, and higher flashpoints than materials such as hydrocarbons, diesel fluid, and gel.

Core holder 15 may include components of a coreflooding system. The components include magnetic field detectors 20. Magnetic field detectors 20 may be installed on sleeve 18. As noted, sleeve 18 holds the core and is transparent to electromagnetic signals. In some implementations, the distance between detectors 20 and core 10 is minimized, since a reduction in this distance may improve measurement accuracy. In this regard, in some implementations, electrical interference among magnetic field detectors may be reduced by placing the magnetic field detectors at least a minimum distance apart. For example, the distance may range from several millimeters to several centimeters. The value of this minimum distance may depend upon parameters such as the percent-by-weight (wt %) of hydrophilic magnetic nanoparticles in the mixture and the distance between the magnetic field detectors and the core.

The magnetic field detectors 20 are configured and arranged to sense a magnitude of the magnetic field produced by the hydrophilic magnetic nanoparticles in the core, a direction of the magnetic field produced by the hydrophilic magnetic nanoparticles as the hydrophilic magnetic nanoparticles travel through the core, or both the magnitude and the direction of the magnetic field. The magnitude and the direction of the magnetic field together define a magnetic field strength vector for the magnetic field. In some implementations, the magnetic field strength vector corresponds to the amount of water present in the core and to the directional flow of the water at a particular time and location. In some implementations, the magnitude of the magnetic field detected by the magnetic field detectors corresponds to a percentage of water present in a region of the core producing to the magnetic field.

Figure 3:
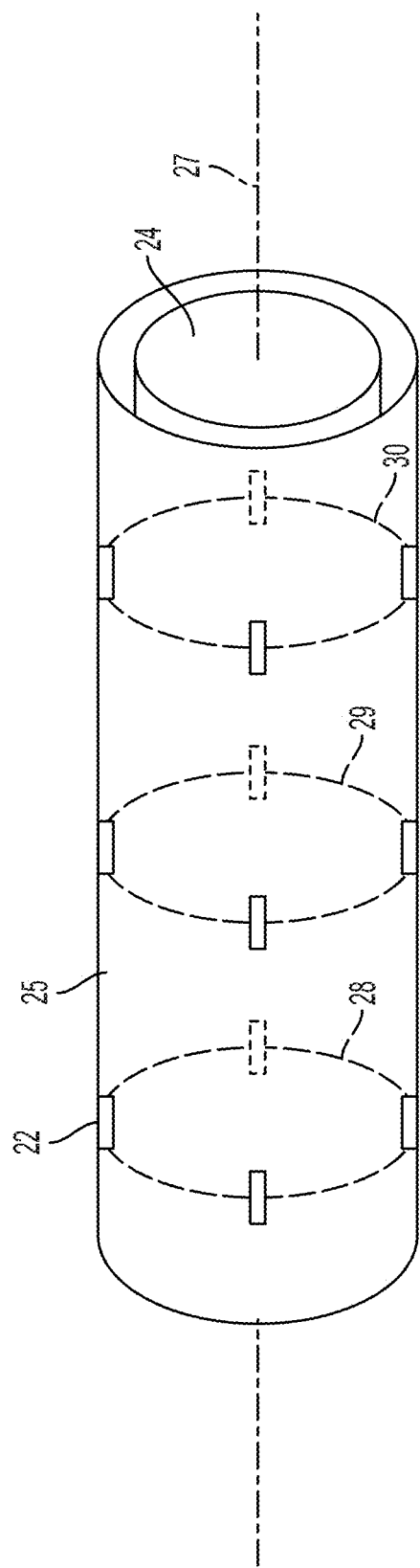
FIG. 3 is a perspective view of an example core holder containing arrays of complementary metal-oxide semiconductor (CMOS) magnetometers.

In the example of FIG. 3, the magnetic field detectors include CMOS magnetometers, one of which is labeled 22. The others are similar in shape, but not labeled. The CMOS magnetometers may be arranged in one or more arrays around a circumference of core 24 on or within a sleeve 25 of the core holder or, alternatively, on its frame. The arrays may be arranged along a dimension along which fluid flows in the core. That dimension is the longitudinal dimension of the core in this example and is represented by dashed line 27. Each CMOS magnetometer may be mounted on a flexible printed circuit board (PCB) on the sleeve. The flexible PCB may be made, for example, of a polyimide film such as Kapton® from DuPont® corporation. In this example, there are twelve magnetic field detectors arrange circumferentially around the core in three arrays 28, 29, and 30 of four each. Each magnetometer is offset 90° from its circumferential neighbors. In other examples, different numbers of magnetic field detectors may be used. For example, there may be two, three, four, five, six, seven, eight, nine, ten, eleven, or thirteen magnetic field detectors arranged spatially around the core. In some implementations, the CMOS magnetometers operate based upon the principle of tunneling magneto-resistance (TMR) to sense, in three dimensions, the magnetic field produced by the hydrophilic magnetic nanoparticles. Accordingly, by using arrays of CMOS magnetometers, it is possible to obtain a three-dimensional magnetic field strength vector during a subject coreflooding experiment.

Figure 4:
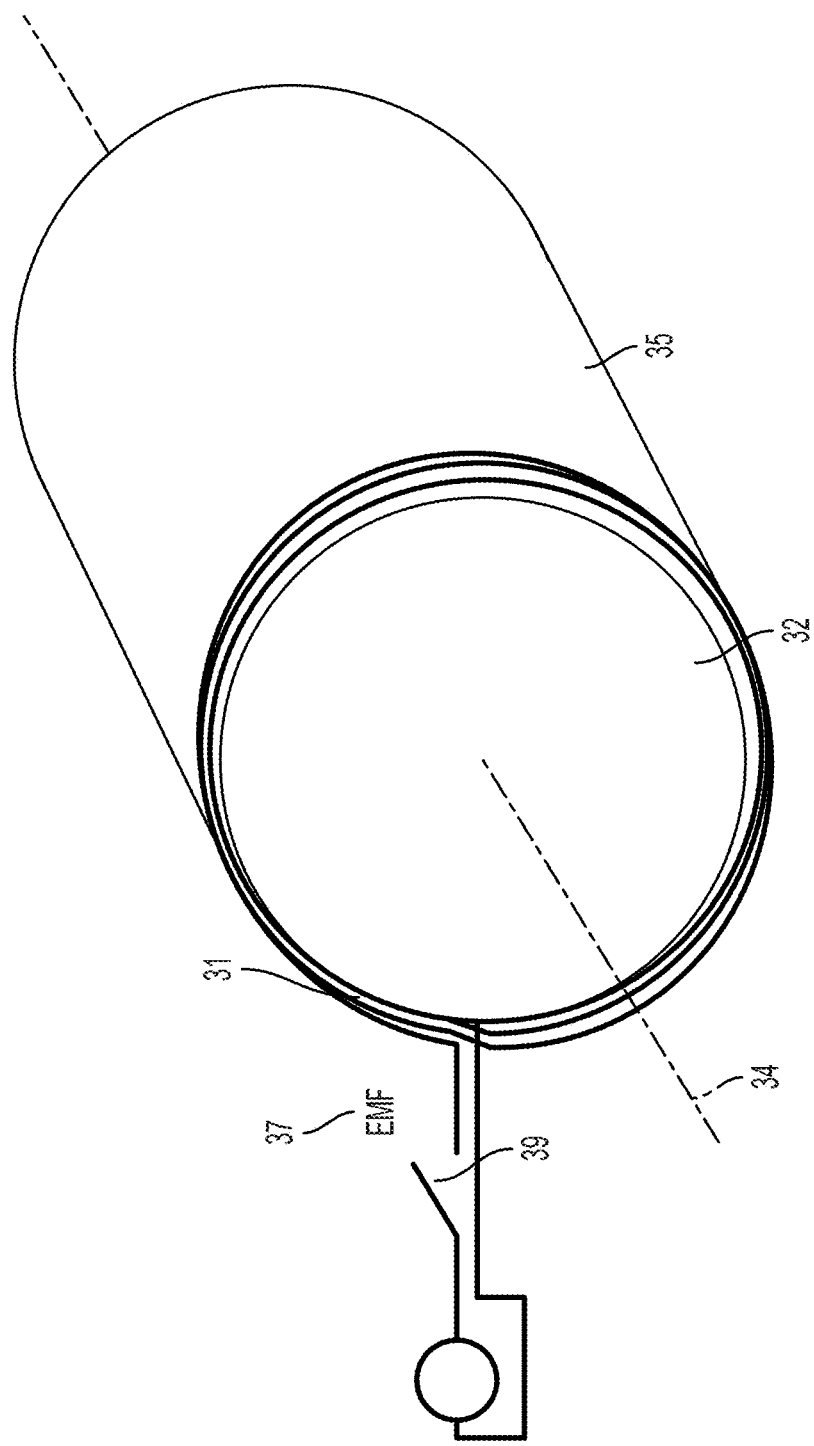
FIG. 4 is a perspective view of an example core holder containing inductively-coupled coil around the core holder.

In the example of FIG. 4, the magnetic field detectors include inductively-coupled coil 31 around a circumference of the core and extending at least party-way along a dimension along which fluid flows in the core 32. This dimension is represented by dashed line 34 and is the longitudinal dimension of the core in this case. In this example, the inductively-coupled coil is disposed on and wound around the exterior of core holder 35. The inductively-coupled coil may be wound around the core holder across an entire longitudinal extent of the core holder. If measurements are to be obtained along only part of the core holder, then the inductively-coupled coil may be wound around that part only. In operation, as the mixture and the hydrocarbon pass through the core, the changing magnetic field induces current in the coil. As a result, an electromotive force (EMF) 37 is generated at terminals 39 of the coil. The resulting voltage produced at the terminals is proportional to the amount to water in the core and to the rate of flow of the fluid through the core. A single inductively-coupled coil may be wound around the core or multiple inductively-coupled coils may be wound around the core. In the case of multiple inductively-coupled coils, multiple sets of measurements may be obtained—one set from each coil. Example inductively-coupled coil 31 may be operate using electrical signals in the kilohertz (kHZ) frequency range through the megahertz (MHz) frequency range.

Figure 5:
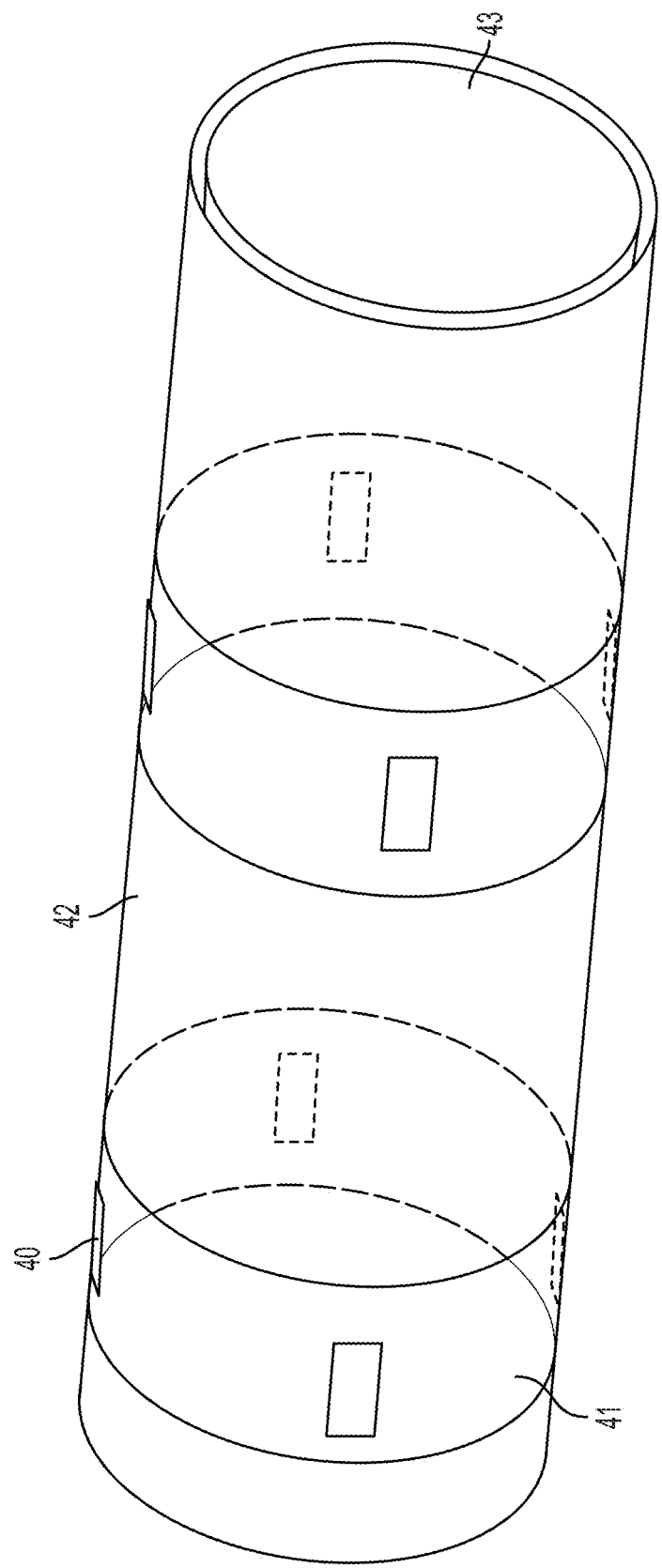
FIG. 5 is a perspective view of an example core holder containing both arrays of CMOS magnetometers and inductively-coupled coil around the core holder.

In the example of FIG. 5, the magnetic field detectors include a combination of one or more arrays of CMOS magnetometers 40 and one or more inductively-coupled coils 41 arranged on core holder 42 around core 43. The CMOS magnetometers and the inductively-coupled coils of FIG. 5 may have the same structures, functions, arrangements, and variations as the CMOS magnetometers and the inductively-coupled coils of FIGS. 3 and 4, respectively. For example, the CMOS magnetometers may be mounted on or within the sleeve of the core holder and the inductively-coupled coils may be mounted to an exterior of the core holder. CMOS magnetometers 40 and inductively-coupled coils 41 may obtain measurements of the magnetic field produced by the hydrophilic magnetic nanoparticles within the core and passing through the core. In cases where two detectors obtain the same measurements, those same measurements may be compared against each other to confirm their accuracy or combined—for example, averaged—to reduce potential measurement errors. When a measurement, such as a three-dimensional magnetic field strength vector, is obtainable from one magnetic field detector only, that measurement may be used without alteration.

Figure 6:
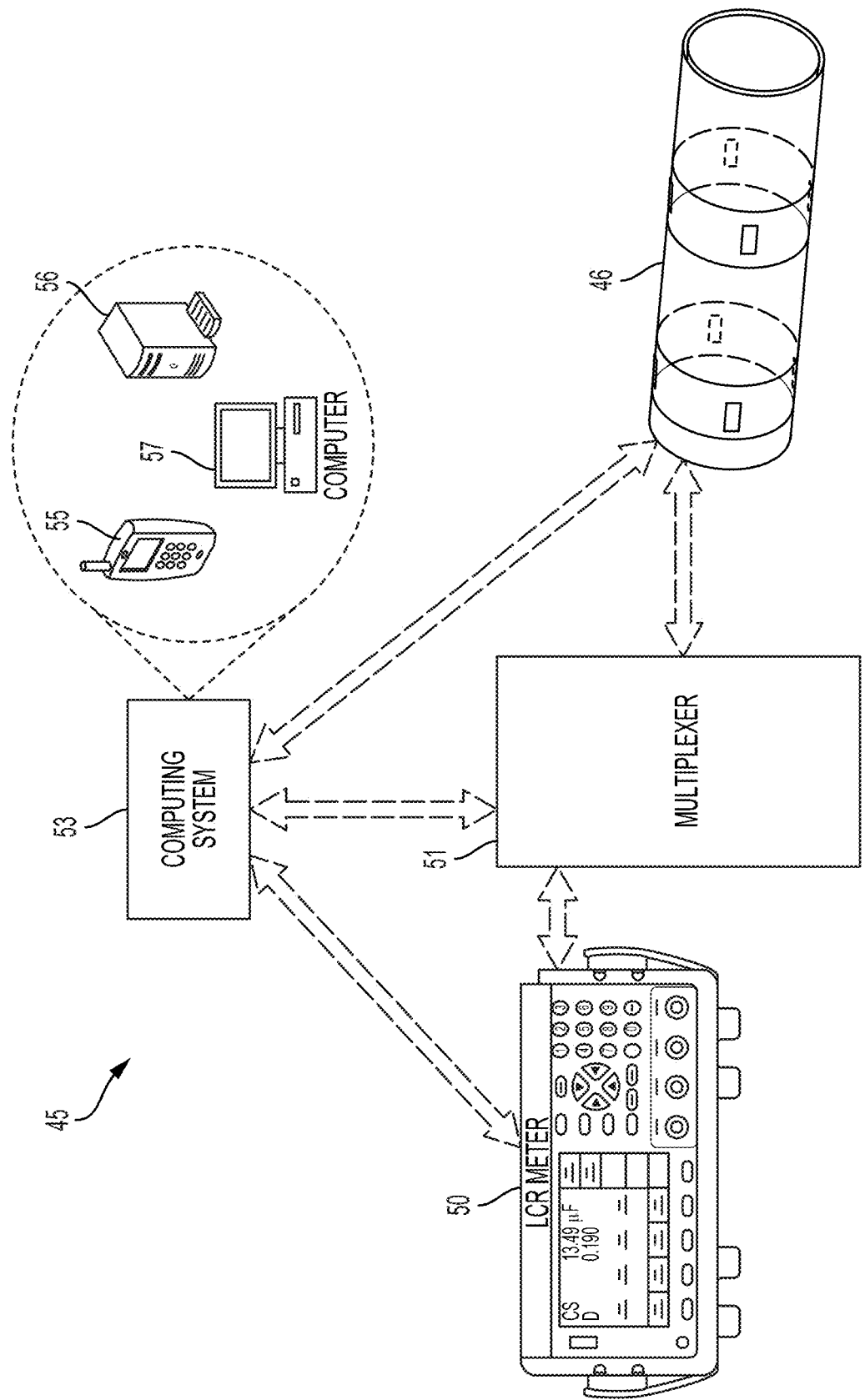
FIG. 6 is a block diagram of an example system for detecting saturation levels of a core and for generating a saturation profile of the core.

FIG. 6 shows an example system 45 that may be used with components of the type shown in FIGS. 2, 3, 4, and 5. The components 46 of FIG. 5 are shown as an example. Although FIG. 5 includes both CMOS magnetometers and inductively-coupled coils, the components used in system 45 may include CMOS magnetometers only as in FIG. 3 or inductively-coupled coils only as in FIG. 4.

In implementations where the magnetic field detectors include one or more inductively-coupled coils, system 45 may employ an LCR (inductance-capacitance-resistance) meter 50. LCR meter 50 may be implemented as a stand-alone instrument as shown or as a component of a data processing system. LCR meter 50 is configured to receive, via a switch such as multiplexer 51, signals from each of the inductively-coupled coils. For example, the LCR meter may receive a voltage across terminals of each of the coils or a current through each of the coils. LCR meter 50 is configured to analyze the signals obtained from the inductively-coupled coils and to output data to computing system 53 based on the signals. The data may represent the voltage across the terminals of the coils or the current through the coils, for example. Computing system 53 may analyze the data received from LCR meter 50 to determine the magnitude of the magnetic field produced by the hydrophilic magnetic nanoparticles in the core. In this regard, the magnitude of the magnetic field at each location may be based on signals received from a coil proximate to that location.

Computing system 53 may be configured—for example, programmed—to communicate with LCR meter 50 and multiplexer 51, as represented by the dashed arrows. Signal transmissions between components 46 and multiplexer 51, between components 46 and computing system 53, and between multiplexer 51 and LCR meter 50 are also represented by dashed arrows. Computing system 53 may include one or more processing devices, such as microprocessors. An example of computing system 53 includes a smartphone 55 alone or in combination with one or more other computing devices, such as server 56 or desktop computer 57. Other examples of computing systems that may be used include those described in this specification.

Computing system 53 may be configured—for example, programmed—to analyze data representing the magnitude of the magnetic field produced by the hydrophilic magnetic nanoparticles. The data may be processed to determine a saturation profile of the core based on the magnetic field. The saturation profile may define a geometric distribution of water along the core over a timescale. A graphical user interface (GUI) representing the saturation profile may be generated by the computing system. The GUI may be rendered on a display device of the computing system or data for the GUI may be sent over a computer network to another device for display. For example, the GUI may be presented on an application (or "app") on a mobile device, such as a smartphone or a tablet computing device, for display. In some implementations, all or some functions of the computing system may be performed by the mobile device.

In implementations where the magnetic field detectors include one or more CMOS magnetometers, system 45 may send signals representing the magnetic field from the CMOS magnetometers directly to computing system 53 or via multiplexer 51 and LCR meter 50. For example, each PCB containing a CMOS magnetometer may include a Bluetooth® transceiver to enable direct wireless communications of the signals between the CMOS magnetometers and the computing system. The Bluetooth® standard was developed by the Bluetooth® Special Interest Group (SIG). Alternatively, the communications may be transmitted over wired media, such as Ethernet. In implementations that include only CMOS magnetometers, the LCR meter and the multiplexer may be bypassed or eliminated from the system altogether.

In implementations where the CMOS magnetometers send signals directly to computing system 53, computing system 53 is configured—for example, programmed—to analyze the signals to determine the magnitude, the direction, or both the magnitude and the direction of the magnetic field produced by hydrophilic magnetic nanoparticles as the hydrophilic magnetic nanoparticles travel through the core. In this regard, the magnitude of the magnetic field at a location may be based on signals received from a single magnetic field detector proximate to that location. The direction of the magnetic field may be based on signals received from two or more magnetic field detectors located along a direction of travel through the core of the hydrophilic magnetic nanoparticles. For example, signals may be obtained from successive magnetic field detectors along the direction of travel. Those signals may be analyzed to identify the change in magnitude of the magnetic field from detector-to-detector. The direction of the magnetic field may be determined based on that change. In some implementations, the direction of the magnetic field may be characterized by a three-dimensional magnetic field strength vector.

Data representing the magnitude and the direction of the magnetic field may be processed by the computing system to determine a saturation profile of the core. As noted, the saturation profile may define a distribution of water along the core over time. A GUI representing the saturation profile may be generated by the computing system. As described previously, the GUI may be rendered on a display device of the computing system or data for the GUI may be sent to an app on a smartphone, tablet, or other mobile device for display. In some implementations, all or some functions of the computing system may be performed on the mobile device.

As noted, in some implementations, the magnetic field detectors may include both CMOS magnetometers and inductively-coupled coils in a single system configuration. In these implementations, signals from the inductively-coupled coils may be routed through the multiplexer and the LCR meter as described previously. In these implementations, signals from the CMOS magnetometers may be sent directly to the computing system wirelessly, or the signals from the CMOS magnetometers may be routed through the multiplexer and the LCR meter via wired or wireless connections.

Computing system 53 may be configured to process data based on the signals received from the CMOS magnetometers and the inductively-coupled coils in the manner described previously. Data representing the magnitude, the direction, or both the magnitude and the direction of the magnetic field may be processed to determine one or more saturation profiles of the core. As described, a GUI representing the saturation profile may be generated by the computing system. As also described, the GUI may be rendered on a display device.

One or more of the LCR meter, the multiplexer, and the magnetic field detectors may be part of a larger data processing system. The larger data processing system may be used to determine pressure and production data from a core during a coreflooding experiment. The data may relate to factors, such as a fluid injection rate into the core, a hydrocarbon production rate of the core, or a cumulative hydrocarbon production of the core over time.

In some implementations, the magnetic fields detected by two or more neighboring magnetic field detectors may be correlated using, for example, a computer-implemented process. For example, it is possible to determine a rate of fluid flow and amount—for example, percentage or fraction—of water in a part of the core based on the correlation of the magnetic fields. In this regard, when two or more magnetic field detectors are in the vicinity of a magnetic particle, all of the magnetic field detectors may sense a magnetic field generated by that particle. This is referred to as interference. However, the way that the sensed magnetic fields change over time can provide an indication about a direction water is traveling through the core, a speed at which the water is traveling through the core, and a content of water contained in an area of the core.

Figure 8:
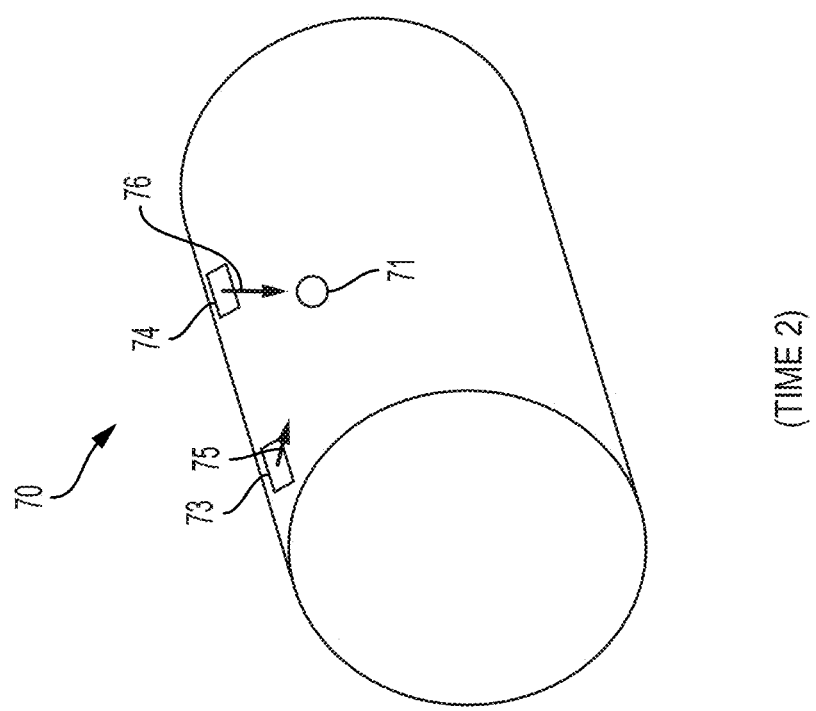
FIG. 8 is a perspective view of an example core at two different times.
Figure 8:
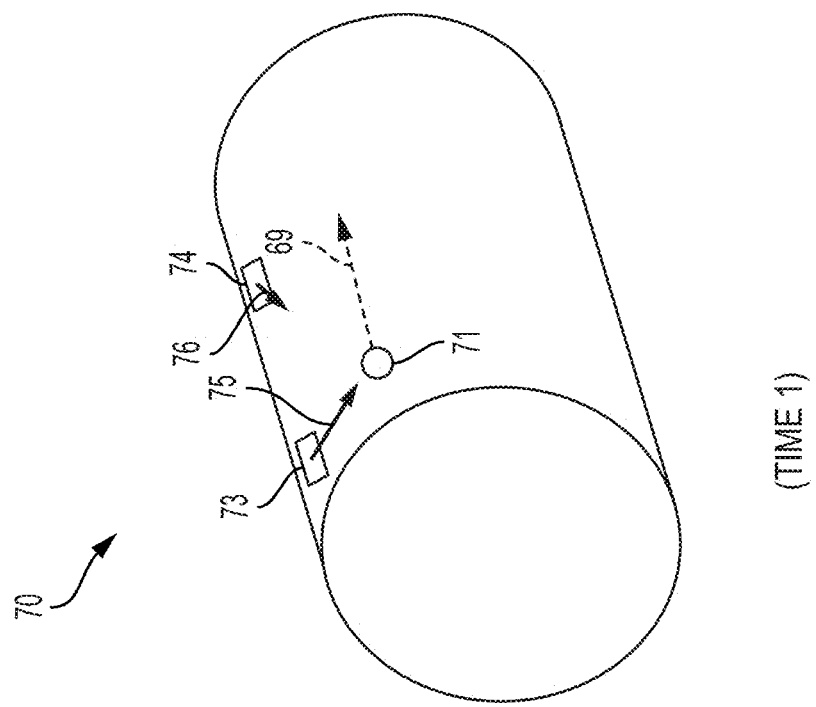

An example correlation process is described with respect to FIG. 8. FIG. 8 shows an example core 70 at two times: "Time 1" and "Time 2". Time 2 is after Time 1. At Time 1, the mixture containing hydrophilic magnetic nanoparticles is forced into the core. An example hydrophilic magnetic nanoparticle 71 is shown. The direction of travel of hydrophilic magnetic nanoparticle 71 is represented by arrow 69. Also shown are two magnetic field detectors 73 and 74 positioned on core 70 as described. Each magnetic field detector 73 and 74 measures a respective magnetic field vector 75 and 76. The magnetic field vectors represent the direction and magnetic field of hydrophilic magnetic nanoparticle 71 as hydrophilic magnetic nanoparticle 71 travels through core 70. As shown, the magnetic field vectors are different for different magnetic field detectors and change for each magnetic field detector as magnetic nanoparticle 71 travels through core 70. An example correlation process includes tracking a change in magnitude and a change direction of the magnetic field vectors of neighboring magnetic field detectors 73 and 74. The change in direction corresponds to the direction of fluid flow through core 70. The magnitude of each magnetic field vector corresponds to the amount of water present proximate to the location. The change in magnitude of each magnetic field vector corresponds to a change in the amount of fluid, such as water, present proximate to the location. A combination of a change in magnitude and a change in direction of the magnetic field vectors corresponds to the speed of the fluid through the core.

Figure 7:
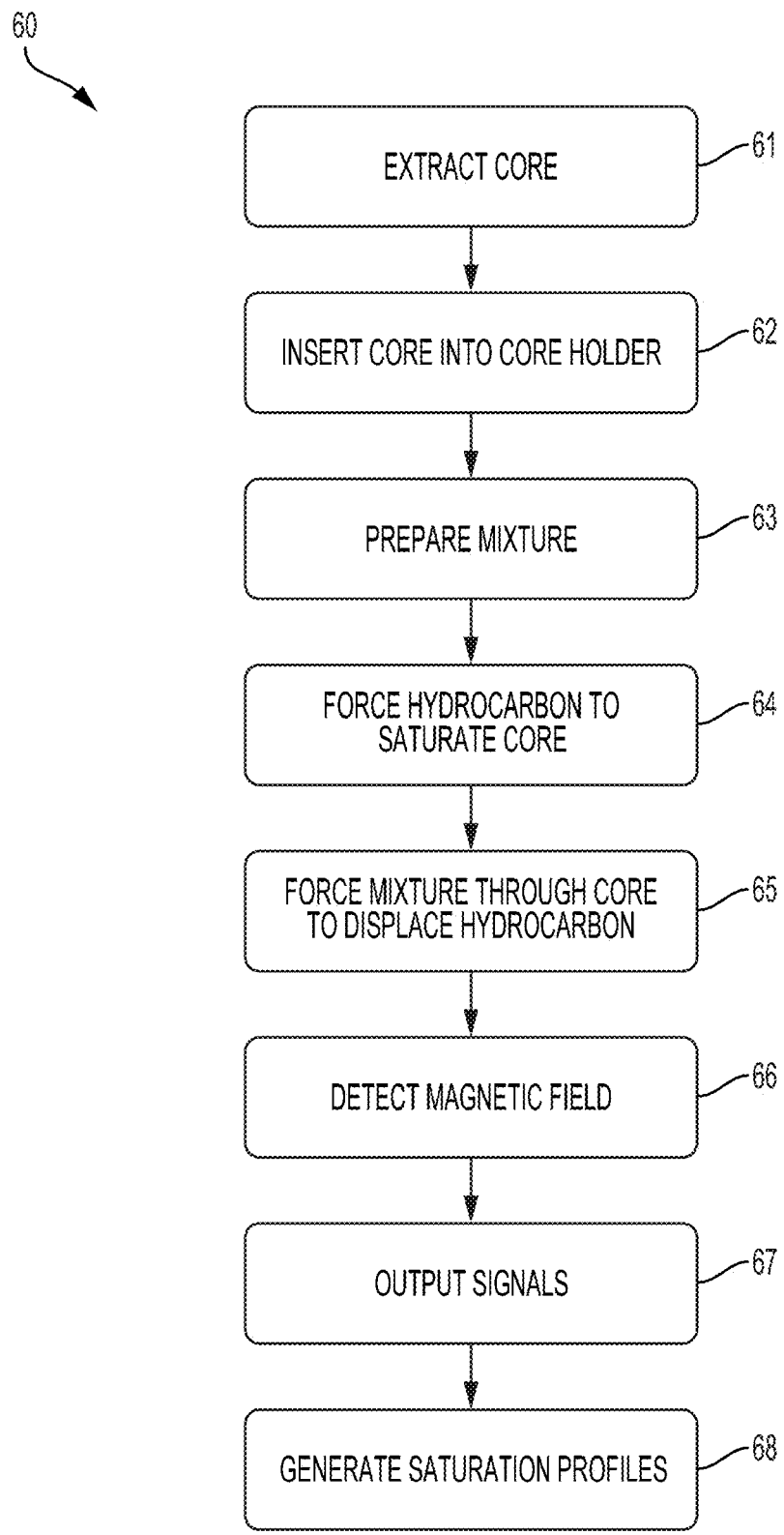
FIG. 7 is a flowchart of an example process for detecting saturation levels of a core and for generating a saturation profile of the core.

FIG. 7 shows an example process 60 that may be performed in conjunction with a coreflooding experiment using the system of FIG. 6. According to process 60, a core is extracted (61) from a formation that has potential to produce hydrocarbon, such as oil or gas. The core is porous and is capable of holding and passing fluid, including hydrocarbon and water. The core is inserted (62) into a core holder. For example, the core may be inserted into a sleeve of the core holder to achieve a conformal fit. Confining liquid, such as water or hydraulic oil, may be pressurized to squeeze the sleeve tightly around the core. In some implementations, the system mimics conditions downhole in a well. Accordingly, the core holder (including the frame and the sleeve) may be configured—for example, constructed—to withstand downhole conditions. Examples of downhole conditions include temperatures on the order of 120° Celsius (C.) and pressures on the order of 5000 pounds per square inch, gauge (PSIG).

A mixture comprised of water and hydrophilic magnetic nanoparticles is prepared (63). Although FIG. 7 appears to imply that the mixture is prepared after extraction of the core, the mixture may be prepared prior to extraction of the core or during extraction of the core. Hydrocarbon, such as oil, gas, or both oil and gas, is injected (64) into the core to saturate the core with the hydrocarbon. The mixture comprised of hydrophilic magnetic nanoparticles is then forced (65) through the core to attempt to displace the hydrocarbon within the core. For example, one or more pumps may be used to force the mixture and the hydrocarbon into the core. The same pump or different pumps may be used to force the hydrocarbon and the mixture into the core. The hydrocarbon and the mixture may be distributed within the core as show in FIG. 1, for example.

The hydrophilic magnetic nanoparticles are dispersed within the water and track the water as the water moves through the core. Accordingly, locations of the hydrophilic magnetic nanoparticles within the core correspond to locations of water within the core. Concentrations of the hydrophilic magnetic nanoparticles within the core correspond to volumes of the water within the core. Movement of the hydrophilic magnetic nanoparticles within the core corresponds to movement of the water within the core. The geometry of the core is known beforehand. As a result, the locations, volumes, and movements of the water within the core may be mapped over time to a geometry of the core to obtain a dynamic saturation profile of the core. The saturation profile is dynamic in the sense that the saturation profile changes as fluid, including the hydrocarbon and the mixture, travel through the core. Thus, the saturation profile includes a temporal component and a spatial component. The spatial component reflects an amount and direction of fluid flow. The temporal component is indicative of a duration of all or part of the spatial component.

As noted, the core holder includes magnetic field detectors that comprise one or more CMOS magnetometers, one or more inductively-coupled coils, or a combination of one or more CMOS magnetometers and one or more inductively-coupled coils. The magnetic field detectors detect (66) the magnetic field produced by the hydrophilic magnetic nanoparticles as the hydrophilic magnetic nanoparticles travel with the water through the core. In the example of FIG. 3, the hydrophilic magnetic nanoparticles travel with water through the longitudinal dimension 27 of the core, which produces changes in magnetic field along that dimension. As described previously, the magnetic field detectors are part of a system, such as system 45 of FIG. 6, for analyzing the magnetic fields to produce a saturation profile for the core.

Signals are output (67) from the magnetic field detectors. As described previously, these signals may be sent to the LCR meter and data generated by the LCR meter may be sent to the computing system, or the signals may be sent directly to the computing system. As noted, the signals may represent the magnitude and direction of the magnetic field produced by the hydrophilic magnetic nanoparticles at locations of the magnetic field detectors. The computing system may process data based on the signals to generate (68) one or more dynamic saturation profiles for the core. If more than one type of magnetic field detector is used—for example, CMOS magnetometers and inductively-coupled coils—different saturation profiles for the same core may be obtained based on data from the different types of magnetic field detectors. If more than one type of magnetic field detector is used, data based on signals from the different types of magnetic field detector may be used to generate a single saturation profile for the core. The saturation profile may be obtained with respect to both distance and time. For example, saturation profiles may be obtained for the spatial extent of the core and during the time that fluid is added to the core. In some implementations, the example system is configured to determine two-phase—for example, oil-water or gas-water—flow saturation profiles for the spatial extent of the core and during the time that fluid is present within the core.

The computing system renders the saturation profiles on a display device or outputs data representing the saturation profiles to a mobile device or to another third party system, as described previously. The data may be output over a computer network or other wired or wireless transmission media.

In some implementations, the magnetic field data obtained by the data processing system represents measurements of magnetic fields in real-time. In this regard, in some implementations, real-time may not mean that two actions are simultaneous, but rather may include actions that occur on a continuous basis or track each other in time, taking into account delays associated with processing, data transmission, hardware, and the like. Accordingly, the saturation profiles generated by the system may represent dynamic representations of the core over time. That is, the saturation profiles may change as fluid is introduced into the core. For example, if the volume of fluid is increased, the saturation profile may change. For example, if the force applied to the fluid is increase, the saturation profile may change.

The example system may be used to implement both steady-state and unsteady-state coreflooding experiments. In unsteady-state coreflooding experiments, the core is saturated with a hydrocarbon, such as oil, and the mixture is injected into the core at an inlet. Following injection of the mixture, only hydrocarbon is produced at an outlet of the core. After a time, both hydrocarbon and the mixture is produced. In steady-state coreflooding experiments, hydrocarbon and the mixture are injected into the core at the inlet. Hydrocarbon and the mixture appear at the outlet roughly commensurate with their injection rate.

All or part of the system and processes described in this specification and their various modifications (subsequently referred to as "the processes") may be controlled at least in part by one or more computing systems using one or more computer programs. Examples of computing systems include, either alone or in combination, one or more desktop computers, laptop computers, servers, server farms, and mobile computing devices such as smartphones, features phones, and tablet computers.

The computer programs may be tangibly embodied in one or more information carriers, such as in one or more non-transitory machine-readable storage media. A computer program can be written in any form of programming language, including compiled or interpreted languages, and it can be deployed as a stand-alone program or as a module, part, subroutine, or unit suitable for use in a computing environment. A computer program can be deployed to be executed on one computer system or on multiple computer systems at one site or distributed across multiple sites and interconnected by a network.

Actions associated with implementing the systems may be performed by one or more programmable processors executing one or more computer programs. All or part of the systems may be implemented as special purpose logic circuitry, for example, an field programmable gate array (FPGA) or an ASIC application-specific integrated circuit (ASIC), or both.

Processors suitable for the execution of a computer program include, for example, both general and special purpose microprocessors, and include any one or more processors of any kind of digital computer. Generally, a processor will receive instructions and data from a read-only storage area or a random access storage area, or both. Components of a computer (including a server) include one or more processors for executing instructions and one or more storage area devices for storing instructions and data. Generally, a computer will also include one or more machine-readable storage media, or will be operatively coupled to receive data from, or transfer data to, or both, one or more machine-readable storage media.

Non-transitory machine-readable storage media include mass storage devices for storing data, for example, magnetic, magneto-optical disks, or optical disks. Non-transitory machine-readable storage media suitable for embodying computer program instructions and data include all forms of non-volatile storage area. Non-transitory machine-readable storage media include, for example, semiconductor storage area devices, for example, erasable programmable read-only memory (EPROM), electrically erasable programmable read-only memory (EEPROM), and flash storage area devices. Non-transitory machine-readable storage media include, for example, magnetic disks such as internal hard disks or removable disks, magneto-optical disks, and CD (compact disc) ROM (read only memory) and DVD (digital versatile disk) ROM.

Each computing device may include a hard drive for storing data and computer programs, one or more processing devices (for example, a microprocessor), and memory (for example, RAM) for executing computer programs. Each computing device may include an image capture device, such as a still camera or video camera. The image capture device may be built-in or simply accessible to the computing device.

Each computing device may include a graphics system, including a display screen. A display screen, such as a liquid crystal display (LCD) or a CRT (Cathode Ray Tube) displays to a user images that are generated by the graphics system of the computing device. As is well known, display on a computer display (for example, a monitor) physically transforms the computer display. For example, if the computer display is LCD-based, the orientation of liquid crystals may be changed by the application of biasing voltages in a physical transformation that is visually apparent to the user. As another example, if the computer display is a CRT, the state of a fluorescent screen may be changed by the impact of electrons in a physical transformation that is also visually apparent. Each display screen may be touch-sensitive, allowing a user to enter information formation onto the display screen via a virtual keyboard. On some computing devices, such as a desktop computer or a smartphone, a physical QWERTY keyboard or Arabic keyboard and scroll wheel may be provided for entering information formation onto the display screen.

Each computing device, and computer programs executed on such a computing device, may also be configured to accept voice commands, and may be configured to perform functions in response to such commands. For example, the process described in this specification may be initiated at a client, to the extent possible, via voice commands.

Elements of different implementations described may be combined to form other implementations not specifically set forth previously. Elements may be left out of the processes described without adversely affecting their operation or the operation of the system in general. Furthermore, various separate elements may be combined into one or more individual elements to perform the functions described in this specification.

Other implementations not specifically described in this specification are also within the scope of the following claims.

What is claimed is:

1. A system comprising:
   magnetic field detectors for spatial distribution across a dimension of a target containing both a hydrocarbon and a mixture comprised of water and hydrophilic magnetic nanoparticles, the magnetic field detectors being configured to detect a magnetic field associated with the hydrophilic magnetic nanoparticles; and
   a data processing system to determine a saturation profile of the target based on the magnetic field,
   where the magnetic field detectors include a plurality of devices placed at discrete points on or in a sleeve of the target,
   where the hydrophilic magnetic nanoparticles are immiscible in crude oil,
   where the system comprises twelve magnetic field detectors arranged circumferentially around the core in three arrays of four magnetic field detectors each, and
   where each magnetic field detector is offset 90 degrees from its circumferential neighbor.

2. The system of claim 1, where the data processing system is configured to perform operations comprising:
   obtaining first data based on the magnetic field, the first data representing a magnitude of the magnetic field and a direction of the magnetic field;
   processing the first data to determine the saturation profile; and
   outputting second data representing the saturation profile.

3. The system of claim 1, where the data processing system is configured to determine, as part of the saturation profile, relative amounts of the hydrocarbon and the water across a dimension of the target, and
   wherein the mixture contains between about 0.2 percent-by-weight (wt %) and about 0.3 wt % of hydrophilic magnetic nanoparticles.

4. The system of claim 1, where the saturation profile comprises a magnitude component and a direction component, the magnitude component being indicative of an amount of water in the target and the direction component being indicative of a direction of flow of the water through the target.

5. The system of claim 1, where the saturation profile comprises a temporal component and a spatial component, the temporal component being indicative of a duration of at least part of the spatial component.

6. The system of claim 1, where the target is surrounded by the sleeve and a frame that are spaced with an annulus;
   where the annulus is filled with a confining liquid;
   where the target is a core of a reservoir formation comprised of porous rock, the core being held by a core holder;
   where the magnetic field detectors are on the core holder; and
   where the sleeve provides a seal around the core.

7. The system of claim 1, where the hydrophilic magnetic nanoparticles have a stronger affinity with the water than with the hydrocarbon.

8. The system of claim 1, where the magnetic field detectors comprise inductively-coupled coil arranged along a dimension of the target along which fluid flows through the target.

9. The system of claim 1, where the magnetic field detectors comprise magnetometers arranged along a dimension of the target along which fluid flows through the target; and
   where magnetometers include complementary metal-oxide semiconductor (CMOS).

10. The system of claim 9, where the CMOS magnetometers are configured to determine, based on the magnetic field, a magnetic field strength vector in three dimensions, the magnetic field strength vector representing changes in magnetic field strength across the target;
  where the CMOS magnetometers operate based upon the principle of tunneling magneto-resistance (TMR); and
  where magnetic fields detected by two or more neighboring CMOS magnetometers are correlated using a computer-implemented process.

11. The system of claim 10, where the magnetic field detectors are mounted on a flexible printed circuit board (PCB) on the sleeve.

12. The system of claim 10, where each printed circuit board (PCB) containing a CMOS magnetometer includes a transceiver to enable direct wireless communications.

13. A method of generating a saturation profile of a target containing a hydrocarbon, the comprising:
  forcing, through the target, a mixture comprised of water and hydrophilic magnetic nanoparticles to produce, within the target, a distribution of the mixture and the hydrocarbon;
  detecting, by magnetic field detectors, a magnetic field associated with the hydrophilic magnetic nanoparticles within the target; and
  generating the saturation profile of the target based on the magnetic field, the saturation profile representing at least part of the distribution,
  where the magnetic field detectors include a plurality of devices placed at discrete points on or in a sleeve of the target,
  where generating the saturation profile comprises determining, as part of the saturation profile, relative amounts of the hydrocarbon and the water across a length of the target, and
  where generating the saturation profile comprises tracking a change in magnitude and a change in direction of magnetic field vectors of neighboring magnetic field detectors, the change in magnitude indicating a change in an amount of the mixture and the change in direction indicating a change in a flow direction of the mixture.

14. The method of claim 13, where generating the saturation profile is performed using a data processing system and comprises:
  obtaining first data based on the magnetic field, the first data representing a magnitude of the magnetic field and a direction of the magnetic field;
  processing the first data to determine the saturation profile; and
  outputting second data representing the saturation profile.

15. The method of claim 13, where the saturation profile comprises a magnitude component and a direction component, the magnitude component being indicative of an amount of water in the target and the direction component being indicative of a direction of flow of the water through the target.

16. The method of claim 13, where the saturation profile comprises a temporal component and a spatial component, the temporal component being indicative of a duration of at least part of the spatial component.

17. The method of claim 13, where the target is surrounded by the sleeve and a frame that are spaced with an annulus;
  where the annulus is filled with a confining liquid;
  where the target is a core of a reservoir formation comprised of porous rock, the core being held by a core holder;
  where detecting is performed by magnetic field detectors are on the core holder; and
  where the sleeve provides a seal around the core.

18. The method of claim 17, where the magnetic field detectors comprise inductively-coupled coil arranged along a dimension of the target along which fluid flows through the target, and
  where the inductively-coupled coils comprise an inductance-capacitance-resistance (LCR) meter configured to receive, via a switch, signals from each of the inductively-coupled coils.

19. The method of claim 17, where the magnetic field detectors comprise magnetometers arranged along a dimension of the target along which fluid flows through the target; and
  where magnetometers include complementary metal-oxide semiconductor (CMOS).

20. The method of claim 19, where the CMOS magnetometers are configured to determine, based on the magnetic field, a magnetic field strength vector in three dimensions, the magnetic field strength vector representing changes in magnetic field strength across the target;
  where the CMOS magnetometers operate based upon the principle of tunneling magneto-resistance (TMR); and
  where magnetic fields detected by two or more neighboring CMOS magnetometers are correlated using a computer-implemented process.

21. The method of claim 13, where the hydrophilic magnetic nanoparticles have a stronger affinity with the water than with the hydrocarbon.

22. The method of claim 13, further comprising:
  performing a correlation process based on the magnetic field to determine at least one of a direction that fluid is traveling through the core, a speed at which the fluid is traveling through the core, or a content of the fluid contained in an area of the core, at least some of the fluid comprising the mixture.

* * * * *